United States Patent [19]
Petry et al.

[11] Patent Number: 5,803,606
[45] Date of Patent: Sep. 8, 1998

[54] SURFACE PHOTOTHERMIC TESTING DEVICE

[75] Inventors: Harald Petry, Saarbrucken; Helmut Prekel, Lindau, both of Germany

[73] Assignee: Phototherm Dr. Petry GmbH, Saarbrucken, Germany

[21] Appl. No.: 637,822

[22] PCT Filed: Dec. 7, 1994

[86] PCT No.: PCT/DE94/01448

§ 371 Date: May 8, 1996

§ 102(e) Date: May 8, 1996

[87] PCT Pub. No.: WO95/16907

PCT Pub. Date: Jun. 22, 1995

[30] Foreign Application Priority Data

Dec. 16, 1993 [DE] Germany .......................... 43 43 076.7

[51] Int. Cl.[6] .................................................. G01N 25/00
[52] U.S. Cl. ............................... 374/45; 374/5; 374/130; 374/161; 374/7
[58] Field of Search .................... 374/161, 159, 374/137, 130, 45, 4, 5, 6, 7

[56] References Cited

U.S. PATENT DOCUMENTS

| | | | |
|---|---|---|---|
| 3,142,755 | 7/1964 | Leroux | 374/159 |
| 4,075,493 | 2/1978 | Wickersheim | 374/159 |
| 4,647,220 | 3/1987 | Adams et al. | 374/5 |
| 4,679,946 | 7/1987 | Rosencwaig et al. | 374/7 |
| 4,729,668 | 3/1988 | Angel et al. | 374/161 |
| 4,874,251 | 10/1989 | Thomas et al. | 374/45 |
| 4,908,835 | 3/1990 | Nishiuchi et al. | 374/45 |
| 5,036,194 | 7/1991 | Hazel | 374/161 |
| 5,052,816 | 10/1991 | Nakamura et al. | 374/5 |
| 5,131,758 | 7/1992 | Heyman et al. | 374/4 |
| 5,350,236 | 9/1994 | Thakur et al. | 374/161 |
| 5,358,333 | 10/1994 | Schmidt et al. | 374/45 |
| 5,374,122 | 12/1994 | Devitt et al. | 374/45 |
| 5,433,106 | 7/1995 | Matsumura et al. | 374/45 |

FOREIGN PATENT DOCUMENTS

| | | | |
|---|---|---|---|
| 0 015 078 | 4/1984 | European Pat. Off. . | |
| 0 279 347 | 8/1988 | European Pat. Off. . | |
| 3439287 | 5/1985 | Germany . | |
| 3504237 | 1/1988 | Germany . | |
| 3913474 | 10/1990 | Germany . | |
| 4003407 | 8/1991 | Germany . | |
| 0161623 | 10/1982 | Japan | 374/161 |
| 0014021 | 1/1983 | Japan | 374/161 |
| 0124938 | 7/1983 | Japan | 374/5 |
| 360250640 | 12/1985 | Japan | 374/159 |
| 0857821 | 8/1981 | U.S.S.R. | 374/6 |
| 1462123 | 2/1989 | U.S.S.R. | 374/161 |
| 81/03704 | 12/1981 | WIPO | 374/7 |
| 8203914 | 11/1982 | WIPO | 374/161 |

Primary Examiner—Diego F. F. Gutierrez
Attorney, Agent, or Firm—Baker & Daniels

[57] ABSTRACT

In a device for photothermically testing a surface (1) of a moving test specimen (2), an excitation beam (5) may be applied to a test area (13). The excitation beam (5) passes through an aperture (12) in a collecting lens (11) that reproduces the thermal radiation generated in a measuring area (14), so that the collecting lens (11) may be adapted to a wavelength of the excitation beam (5) passed to a detector (20). A coupling mirror (9) mounted in the path of excitation beam (5) has practically total reflectivity for the wavelength of the excitation beam (5) and is arranged in such a way that it is very small near the focal area of the excitation beam (5), so that together with the aperture (12) of the collecting lens (11) it only masks a small part of the thermal radiation (17) passed to the detector (20). In another embodiment, the excitation beam (5) falls directly on the surface (1) through an aperture in the decoupling mirror that deflects the thermal radiation, whereas the thermal radiation can be passed with practically all is intensity to the detector (20) through the decoupling mirror with appropriate reflectivity.

2 Claims, 2 Drawing Sheets

1 SURFACE
2 TEST SPECIMEN
3 ARROW
4 EXCITATION LASER
5 EXCITATION LASER BEAM
6 DEFLECTION MIRROR
7 CONTROL MIRROR
8 EXCITATION FOCUSING LENS
11 COLLECTING LENS
12 APERTURE
13 TEST AREA
14 MEASURING AREA
15 ANGULAR AREA
16 SIGNAL BEAM
17 PARALLEL BEAM
18 DETECTOR LENS
19 FILTER
20 DETECTOR
21 DECOUPLING MIRROR
22 CYLINDRICAL BORE
23 REFLECTION SURFACE

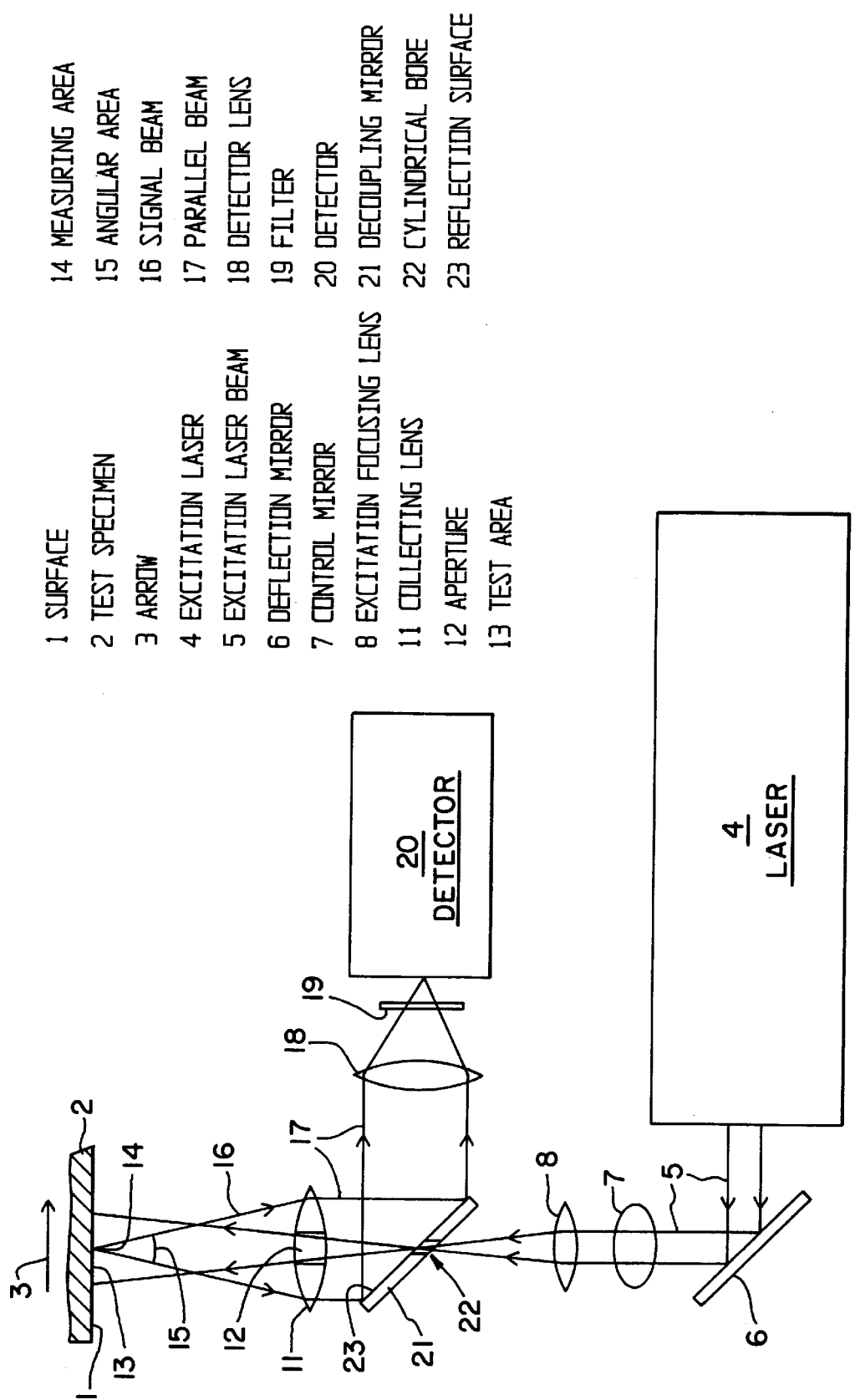

SURFACE PHOTOTHERMIC TESTING DEVICE

BACKGROUND OF THE INVENTION

The present invention relates to a device for photothermic testing of a surface, and more particularly to photothermic testing of a moving test specimen. The present invention includes an illuminating device capable of generating an intensity-modulated excitation radiation and an optical system for applying the excitation radiation to a surface of a moving test specimen. The system is capable of passing thermal radiation given off by a measuring area to a detector, which thermal radiation is captured in an angular area enlarged relative to the direct field of view of the detector. The optical system features a reflection device having a reflection surface which allows coaxial alignment of the excitation radiation emitted from the illuminating device with the thermal radiation passed to the detector. The present invention features an imaging device disposed between the surface of the test specimen and the detector. The imaging device collects that portion of the thermal radiation emitted from the test area situated in the focal area of the imaging device.

A device of the general category of the present invention is previously known from DE 39 13 474 A1. DE 39 13 474 A1 discloses a neodym/YAG laser illuminating device which allows focusing an intensity-modulated excitation radiation in a parallel beam. The optical system comprises a first and second deflection mirror and an imaging lens, which direct the excitation radiation to a surface of a test specimen within a test area. The first deflection mirror deflects the excitation radiation exiting from the neodym/YAG laser onto the second deflection mirror. Thermal radiation in the infrared spectral range between about 2 $\mu$m and 5 $\mu$m is given off by the surface of the test specimen and such radiation is of a longer wavelength than the excitation radiation. Some of thermal radiation emitted from the test specimen can be transmitted from the measuring area to the imaging lens and further transmitted as a parallel beam. The portion of the thermal radiation passing through the imaging lens is deflected by the second deflecting mirror, which reflects both the excitation radiation and the thermal radiation, and then passes through the first deflecting mirror, which is partially translucent for the spectral range of the thermal radiation. The thermal energy then falls on a third deflecting mirror of the optical system, which third mirror is optimized for the spectral range of the thermal radiation. The part of the thermal radiation deflected by the third deflecting mirror falls via a focusing detector lens on a detector.

In this device, the second deflecting mirror is fashioned as a movable scanner, so that the excitation radiation can sweep the surface along a predetermined, or "meandering," measuring path. Because the thermal radiation transmitted by the imaging lens and the excitation radiation are coaxially aligned, the measuring area substantially matches the test area. The imaging lens is traversed by both the excitation radiation and the thermal radiation and is able to transmit both the excitation radiation and the thermal radiation. The imaging lens preferably has a coating on the side of the lens surface which faces the test surface. This coating acts as a window for a spectral range of about 2 $\mu$m to 5 $\mu$m, but is not able to transmit smaller wavelengths, such as the 1 $\mu$m wavelength of the excitation radiation. The first deflecting mirror is maximally reflective for the spectral range of the excitation radiation and at the same time, maximally able to transmit the spectral range of the thermal radiation.

While DE 39 13 474 A1 discloses an imaging lens which functions as a double lens for the excitation radiation and the thermal radiation and therefore captures a large part of the thermal radiation reflected by the surface, the fabrication expense for such an imaging lens is relatively high. Furthermore, using a semipermeable dielectric, or dichroic mirror as the first deflection mirror causes inevitable losses both of excitation radiation intensity and thermal radiation intensity. With closely adjacent spectral ranges, like the excitation radiation and the thermal radiation of the present invention, relatively high losses at partial reflection and partial transmission can be expected. Under these conditions, a testing device with a relatively low output power from the illuminating device relative to the signal intensity is unfavorable.

EP 0 279 347 A2 discloses a device for measuring the displacement of an object wherein a parallel measuring beam is directed to a test specimen via a deflection mirror arranged on the axis of an imaging lens. After hitting the deflection mirror, the beam passes through an aperture disposed in the center of the imaging lens, and in turn the beam falls on the test specimen. The imaging lens is provided with a masking device on one of its sides. The masking device is apertured in the near-axis area and notched in the marginal areas, whereby light reflected by the test specimen passes through the imaging lens, then through the marginal apertures and finally falls on an areal detector. The output signal of the areal detector is then processed to determine the displacement of the test specimen.

DE 40 03 407 A1 teaches a device wherein an intensity-modulated excitation radiation generated by a laser enters one end of a fiber optics bundle. Provided on the other end of the fiber optics bundle, near the test specimen, is a cross section converter by which the exiting excitation radiation can be projected on the surface by using a cylindrical lens through a tilted semi-translucent mirror. The mirror deflects part of the emitted thermal radiation to a detector.

This device allows a simple adaptation of the test area to different measuring conditions by using a cross section converter and a cylindrical lens. However, using the semi-translucent mirror for separating the excitation radiation from the thermal radiation involves unsuitably high losses of at least one of the two radiations.

Known from DE 35 04 237 C2 is an atomic fluorescence spectrometer wherein a parallel excitation beam from a frequency-doubled dye laser in the ultraviolet spectral range is beamed in a specimen cuvette through an aperture of an observation mirror. The excitation radiation induces fluorescent radiation in the atoms examined in the cuvette, and is deflected by the observation mirror opposite to the direction of incidence of the excitation radiation and coupled in a detection device by an observation lens.

Because this device fashions the specimen cuvette as a tube and thus deflects the exiting fluorescent radiation in a longitudinal direction through the observation mirror, a high sensitivity is accomplished. However, measurements of local resolution are not possible with a device of this type, because of averaging over a relatively large measuring volume, both in the excitation and observation of the fluorescent radiation.

Known from EP 0 105 078 A1 is a device for photothermic testing of a surface with a test head to which excitation radiation is fed by way of a fiber optic and where the thermal radiation given off by the surface is passed to a detector having another fiber optics arrangement. The radiations carried by the fiber optics arrangement can be coupled and decoupled using lenses. The test head features a dichroic mirror for superimposition and separation of excitation radiation and thermal radiation. An imaging lens, on which falls the excitation radiation, serves to focus the excitation radiation on the surface and to collect the thermal radiation given off by the surface.

With this device, movement of the test head across the surface for local-resolution measurements is relatively simple because fiber optics for carrying the radiations are provided. However, unfavorably high losses of usable radiation are incurred because of coupling and decoupling losses and through providing the dichroic mirror.

Known from DE 34 39 287 A1 is a device for the optically induced generation of particles to be detected, wherein the excitation radiation from a laser can be deflected to an imaging lens by using a deflecting mirror provided having a centered aperture. The imaging lens, in turn, focuses the excitation radiation on a surface of the specimen being examined. The imaging lens also possesses a centered aperture, which allows particles produced by the excitation radiation, such as electrons or ions, to proceed opposite to the direction of incidence of the excitation radiation. Thus, the particles flow through the apertures of the imaging lens and reflecting mirror to an analyzing device. The apertures of the deflecting mirror and imaging lens must be relatively large as compared to their diameter in order to analyze the particles of a relatively large spatial angular area. An unfavorable consequence thereof is that the excitation radiation assumes Gaussian beam profile. More suitably, a double-humped beam profile is provided where the center minimum coincides with the position of the apertures, thereby reducing the intensity loss of excitation radiation as compared to a Gaussian beam cross section.

While with this device the unfavorable effect of the centered apertures of the deflection mirror and the imaging lens is reduced by selecting a double-humped beam cross section, such entails an uneven illumination of the test area.

SUMMARY OF THE INVENTION

The present invention overcomes the above-noted drawbacks of the prior art by providing a device characterized by an even illumination of the test area as well as a high overall efficiency. The objective of the invention is to provide a device different than the type initially described, in that the present invention employs notably spectrally closely adjacent frequency ranges of the excitation radiation and the emitted thermal radiation.

The objective of the present invention is accomplished by providing an optical system featuring: a focusing device which is acted upon only by the excitation radiation; a reflection surface of the reflecting device which has a reflectivity that is optimized for one of the excitation radiation and the thermal radiation and substantially traversed by the other one of the excitation radiation and the thermal radiation; an imaging device having an aperture through which passes the homocentric excitation radiation; and the focusing device is positioned so that its focal range is between the test surface and one of the detector and the focusing device, so that the excitation radiation falls in divergent fashion on the test surface and the test area is greater than the measuring area.

One advantage of the present invention is that the focusing device, the reflection device and the imaging device are each acted upon by only one of the radiations for generating a measuring signal. As such, each of these optical components can be optionally configured for just that one radiation, namely excitation radiation or thermal radiation. Therefore, either reflectivity or translucence, whichever the case may be, can be maximized without requiring compromises such as, for example, semi-translucent mirrors which allow superimposition of the excitation radiation and thermal radiation.

Another advantage of the present invention is that the focal range of the focusing device is situated between the surface and the focusing device. Thus, the test area—besides achieving a homogeneity in irradiating achieved by the arrangement of the aforementioned optical components in irradiating the test area—is relatively large as compared to the measuring area, so that, notably with moving test specimens, a suitable, large-area action upon the test area is accomplished with the excitation radiation.

Another advantage of the present invention is that informative results are obtained even with test specimens having high moving velocities. This is because of the large-area irradiation of the test area described above, and by pre-irradiating the future measuring area with a few test impulses of the excitation radiation.

Yet another advantage of the present invention is that it allows changing either the wavelength of the excitation radiation or the wavelength range of the thermal radiation captured without large expense. This is so because, by decoupling the excitation beam and the reflected captured thermal radiation, only one set of optical components need to be exchanged.

Another advantage of the present invention is that the aperture fashioned in the imaging device is very small and the portion of thermal radiation captured by the imaging device is therefore reduced only slightly by the aperture disposed therein. Additionally, a related advantage is that losses caused by that part of the reflection surface which blocks a portion of the thermal radiation are minimized. These advantages are accomplished by arranging the focusing device such that its focal range is situated essentially on a line extending coaxially with the center of the reflection device and the imaging device.

In one exemplary embodiment of the invention, the reflection device is a small coupling mirror whose dimensions substantially match the size of the aperture in the imaging device. The excitation radiation falls on the coupling mirror, and the coupling mirror is substantially completely reflective for the wavelength of the excitation radiation. The coupling mirror is arranged on the optical axis of the imaging device, so that the masking areas for the thermal radiation formed by the aperture in the imaging device and the reflection surface of the coupling mirror essentially coincide. The thermal radiation can be passed directly to the detector by way of the imaging device and a detector lens.

In another exemplary embodiment, the coupling device is a decoupling mirror with a cylindrical bore disposed therein. The bore of the decoupling mirror and the aperture of the imaging device are situated on the optical axis of the imaging device and are approximately equal in size. The excitation radiation passes through the bore in the decoupling mirror. The imaging device essentially completely illuminates the decoupling mirror with the thermal radiation captured from the measuring area. The decoupling mirror is adjusted such that the thermal radiation falling on it is further directed to a detector lens, then to the detector. The reflection properties of the decoupling mirror are adapted to the frequency range of the usable thermal radiation and effect a substantially complete reflection, or transmission of the thermal energy, so that substantially the entire usable portion of the thermal radiation captured by the imaging device can be passed to the detector.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

DETAILED DESCRIPTION OF THE INVENTION

Figure 1:
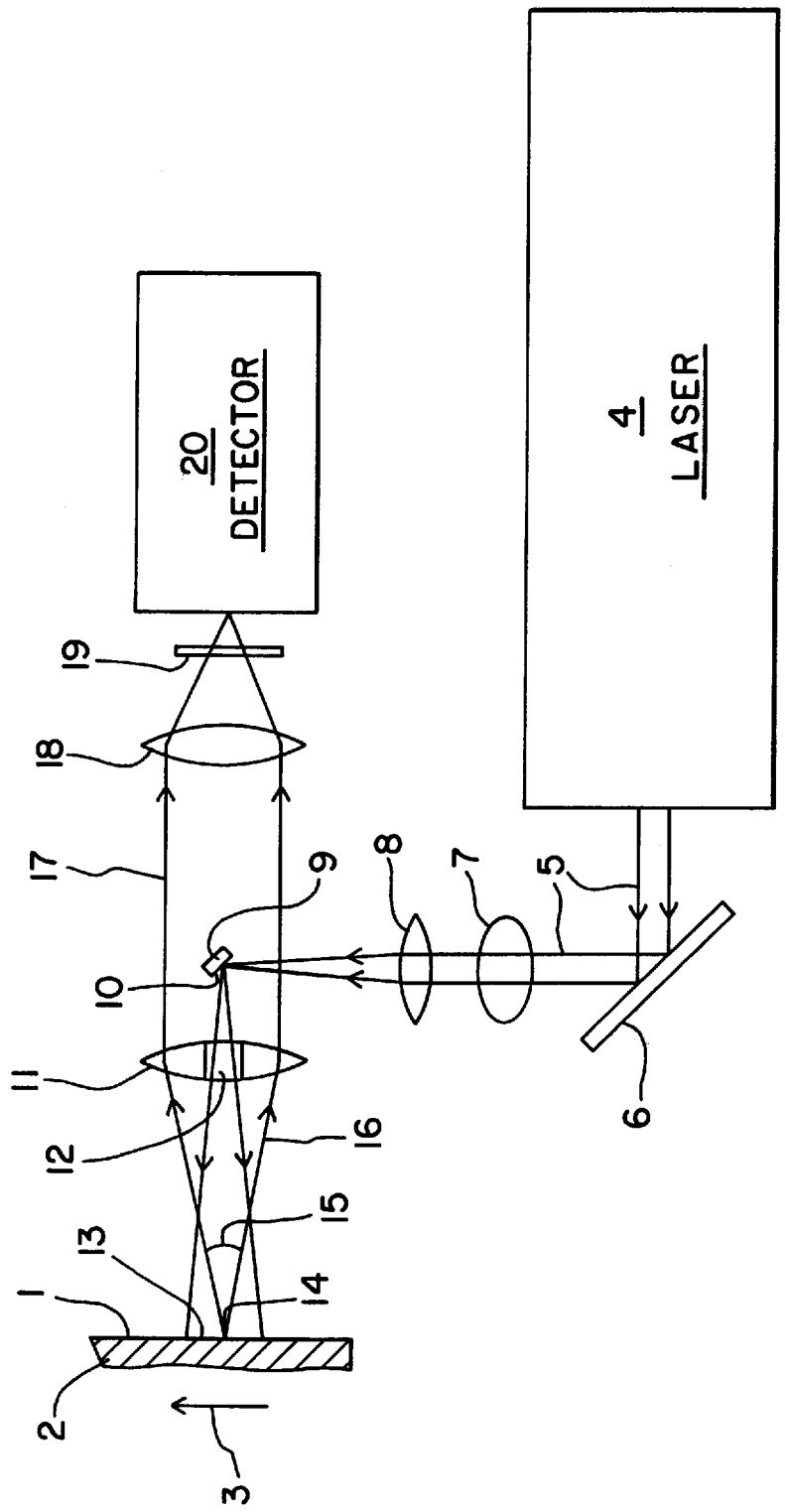
FIG. 1 schematically shows an embodiment of the present invention wherein a signal beam is coaxially superimposed by a decoupling mirror on an excitation beam, and FIG. 2 schematically shows another embodiment of the present invention wherein a signal beam can be separated from the excitation beam.

FIG. 1 schematically shows a device for photothermic testing of a surface 1 of a moving test specimen 2. Test specimen 2 has on its surface 1, e.g., a lacquer layer with a nominal thickness of about 100 μm, its actual thickness to be determined before further processing in a production line along which the test specimen 2 is moved in a direction marked, e.g., by arrow 3, at a velocity of about 2 meters per second.

An excitation laser 4, for example a $CO_2$ laser, emits in the infrared spectral range at about 10 μm an intensity-modulated excitation beam 5. Excitation beam 5 is deflected 90 degrees by a deflection mirror 6 and traverses a control mirror 7 which, relative to the direction of excitation beam 5, is slanted. Mirror 7 couples, by using a control laser (not shown), visible light coaxially in the excitation beam 5. Thus, the infrared light of excitation beam 5, which is invisible to the human eye, has visible light superimposed, thereby increasing operational safety. Control mirror 7 transmits essentially the entire intensity of excitation beam 5, the intensity of the control laser being so chosen that it will not noticeably contribute to the measuring signal.

Upon traversing control mirror 7, excitation beam 5 passes through an excitation focusing lens 8 in the focal range of which coupling mirror 9 is provided. Reflection surface 10 of coupling mirror 9 is provided with a coating which for the wavelength of excitation beam 5 is substantially completely reflective. In other words, the reflectivity of surface 10 is optimized for the wavelength of the excitation energy. The distance between excitation focusing lens 8 and coupling mirror 9 is so chosen that the area of narrowest beam cross section of excitation beam 5 is situated preferably several millimeters in beam direction behind reflection surface 10, thereby avoiding any direct focusing on coupling mirror 9 that might damage the coating on reflection surface 10.

Coupling mirror 9 allows excitation beam 5 to pass through centered aperture 12 disposed in imaging device 11, which device is shown as a collection lens in FIG. 1, so that excitation beam 5, divergent in this area, evenly illuminates surface 1 of test specimen 2 in test area 13. For greater clarity (but not illustrated full-scale), the size of aperture 12 as shown in FIG. 1, is so selected that approximately 98 percent of the intensity of excitation beam 5, based on the intensity reflected by coupling mirror 9, falls on surface 1 in the test area 13. The divergent routing of excitation beam 5 after passing through imaging device 11 represents a considerable contribution to laser protection.

In an variant of the above-described embodiment, aperture 12 in imaging device 11 is provided with a safety closure which, for the frequency range of excitation beam 5, is essentially completely translucent. The safety closure serves to prevent, when the device is used in environments polluted by airborne dust, any harmful entrance of dust through aperture 12 in the device, which device usually is protected by a housing.

The intensity of excitation beam 5 is in this exemplary embodiment modulated with a frequency of a few 100 Hz at a pulse width repetition rate of about 1:1. Part of the incident energy of excitation beam 5 is re-emitted as thermal radiation from the test area 13, due to interaction with the surface 1 of test specimen 2. Depending on the film thickness and material properties in the surface area, a characteristic time progression of the re-emission results.

The portion of the thermal radiation reflected from the measuring area 14 and then captured by imaging device 11 is represented in FIG. 1 in spatial angular area 15. Imaging device 11 is configured for maximum transmission in the spectral range of the thermal radiation being emitted by measuring area 14. The ratio of test area 13 size to measuring area 14 is so selected that at a given velocity of test specimen 2 and about 10 measuring periods, the measuring areas 14 fall in the test area 13 illuminated by the first impulse of excitation radiation 5.

The imaging device 11 is positioned a distance from surface 1 that essentially matches the focal length of device 11, whereby divergent signal beam 16, re-emitted from the measuring area 14, is transformed into parallel beam 17. The size of aperture 12 in imaging device 11 and the size of coupling mirror 9 that masks part of the parallel beam 17 are essentially equal so as to minimize the losses of usable thermal radiation from signal beam 16 and parallel beam 17. Thus, thermal radiation substantially traverses coupling mirror 9 while excitation laser beam 5 is essentially completely transmitted by mirror 9.

The thermal radiation portion carried in parallel beam 17 is via a detector lens 18 and via a filter 19 passed to a detector 20. Filter 19 has a transmission range that differs from the wavelength of excitation beam 5 and ranges in the present exemplary embodiment at about 2 μm to 5 μm. Thus, the intensity of excitation beam 5 reflected back by the surface 1 can be barred by filter 19 from detector 20.

Detector 20 connects to a processing electronics array not illustrated in FIG. 1, which detects the rise in intensity and the phase shift of the maximum intensity of the thermal radiation relative to the impulses of excitation beam 5. These values allow in a manner known in the art the determination of the superficial film thickness of surface 1. Co-linear arrangement of excitation beam 5 and signal beam 16 and respectively parallel beam 17 guarantees that changes in the distance between test specimen 2 and, for example, imaging device 11, will not affect the phase shift between the maximum intensity of the thermal radiation and the impulses of excitation beam 5.

In a variant of the exemplary embodiment illustrated in FIG. 1, coupling mirror 9 features a base that extends across the entire beam cross section of parallel beam 17 and passes essentially completely the utilizable spectral range of the thermal radiation. The reflection surface 10 of coupling mirror 9 is provided in the area of incidence of excitation beam 5 on the base. This variant has the advantage that mounting devices not illustrated in FIG. 1 and holding the base can be arranged outside the parallel beam 17, thus causing no additional masking of parallel beam 17.

FIG. 2 shows schematically a preferred exemplary embodiment of a device for photothermic testing of a surface 1, with items corresponding in FIG. 1 and 2 being referenced identically. In FIG. 2, excitation beam 5 substantially traverses a decoupling mirror 21 through a cylindrical bore 22, which coupling mirror is arranged in the focal range of excitation beam 5. By arranging decoupling mirror 21 in the focal range of excitation beam 5, the size of bore 22 is minimized. The arrangement of decoupling mirror 21 is such that the parallel beam 17 produced by imaging device 11, shown as a collecting lens in FIG. 2, can be substantially completely transmitted by mirror 21, such that parallel beam 17 is deflected essentially at 90 degrees by mirror 21 onto the detector lens 18. Excitation beam 5 falls, after traversing excitation focusing lens 8, directly onto surface 1, thereby minimizing the need for excitation beam 5 to be redirected by a reflection surface. Such an arrangement is advantageous whenever the intensity of excitation beam 5 amounts to several watts, in which case arranging a mirror near the focal range of excitation beam 5 could result in damage to a contaminated reflection surface.

Thus, it can be understood that coupling mirror 9, with reflection surface 10, required in the configuration according to FIG. 1, is dispensable in the arrangement relative to FIG. 2. A change in wavelength of excitation beam 5 involves therefore only the replacement of deflection mirror 6, control mirror 7 and excitation focusing lens 8. Furthermore, any interfering holding elements of coupling mirror 9 are dispensable too.

Similar to the embodiment of FIG. 1, in the embodiment of FIG. 2, the portion of the thermal radiation reflected from the measuring area 14 and then captured by imaging device 11 is represented in FIG. 2 in spatial angular area 15. Imaging device 11 is configured for maximum transmission in the spectral range of the thermal radiation being emitted by measuring area 14. Aperture 12 in imaging device 11 and bore 22 in decoupling mirror 21 are suitably given essentially the same size, so that the masked areas of signal beam 16 are essentially identical and overall losses are minimized. Thus, mirror 21 transmits thermal radiation from beam 17 to lens 18 substantially completely. The reflection surface 23 of decoupling mirror 21 is configured for an optimum reflection of the utilizable spectral share of thermal radiation, the signal yield being increased further by arranging the decoupling mirror 21 in the blurred range of detector lens 18.

In a variant of the exemplary embodiment illustrated in FIG. 2, decoupling mirror 21 features a continuous base whose reflection surface 23 is apertured in the area where excitation beam 5 passes through. The base of decoupling mirror 21 essentially allows complete passage of excitation beam 5. This variant avoids a relatively expensive fashioning of a bore 22 in decoupling mirror 21. This variant is suitable with an intensity of the focal range of focusing lens 8 that is not liable to damage the base of decoupling mirror 21.

In a further, not illustrated embodiment, decoupling mirror 21 is movable in the direction of the axis of excitation beam 5, so that the bore 22 can be positioned in the focal range of excitation focusing lens 8, with detector lens 18 and detector 20 being adaptable. In this embodiment, the size of bore 22 is minimized to the cross section of excitation beam 5 in the focal range of excitation focusing lens 8. Decoupling mirror 21 is tiltable in this configuration, allowing eccentric arrangement of measuring area 14 relative to test area 13. This allows, for example at high velocities of the test specimen of up to 200 meters per minute, setting a maximum lead of test area 13 relative to measuring area 14, thus safeguarding a sufficient heating up of surface 1 of test specimen 2 in order to obtain informative measuring results. Displacement of decoupling mirror 21 ensures additionally that the optical relations in the test area 13 and measuring area 14 will not change, as opposed to an adjustment of the excitation focusing lens 8, which basically is possible as well.

In the exemplary embodiment illustrated in FIG. 1 and 2, excitation focusing lens 8 is a biconcave lens with a focal length of about 50 millimeters. Aperture 12 in imaging device 11, shown as a collecting lens, is in these exemplary embodiments essentially circular. Coupling mirror 10 according to the exemplary embodiment relative to FIG. 1 is a round mirror, and bore 22 of decoupling mirror 21 according to the exemplary embodiment illustrated in FIG. 2 is a circular bore. Test area 13 is circular, so that measurements can be carried out at any direction of movement of test specimen 2.

In applications of the devices where the test specimen 2 moves in only a single fixed direction, the excitation focusing lens 8 is a cylindrical lens. Aperture 12 in imaging device 11 and bore 22 in decoupling mirror 21, as well as decoupling mirror 9, are adapted to the oblong focal area of the cylindrical excitation focusing lens 8, by a similarly oblong shape. Thus, essentially the entire intensity of excitation beam 5 falls on the surface 1 of test specimen 2 in an oblong test area 13.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

We claim:

1. Device for photothermic testing of a surface of a notably moving test specimen, the device comprising:
    an illuminating device for producing an intensity-modulated excitation radiation;
    an optical system for applying the excitation radiation to a test area on the surface and transmitting a portion of thermal radiation given off by a measuring area of the surface to a detector, the portion represented by an angular area;
    a reflection device with a reflection surface with which the excitation radiation and the thermal radiation passed to the detector can be aligned coaxially;
    a focusing device acted upon only by the excitation radiation operatively associated with the illuminating device;
    an imaging device disposed between the surface and the detector along a path of the thermal radiation;
    the imaging device having an aperture through which passes the excitation radiation;
    the imaging device collecting the thermal radiation emitted from the measuring area situated in a focal range of the imaging device;
    the reflection surface of the reflection device having a reflectivity optimized for one of the excitation radiation and the thermal radiation, whereby the radiation for which the reflectivity is optimized is substantially completely reflected and the reflection device is substantially traversed by the other one of the excitation radiation and the thermal radiation; and
    a focal range of the focusing device is situated between the surface and the focusing device, thereby causing the excitation radiation to fall on the surface in divergent fashion.

2. The device according to claim 1, wherein:
    the reflection device is a mirror on whose reflection surface falls essentially the entire portion of the thermal radiation captured by the imaging device;

the reflection surface is a surface of the mirror;

the reflection surface is substantially completely reflective for the utilizable spectral range of the thermal radiation;

the mirror has a cylindrical bore disposed in an area coinciding with the passage of the excitation radiation; and the aperture in the imaging device has a maximum size corresponding to a cross-sectional area of the cylindrical bore, whereby thermal radiation masked by the aperture and the cylindrical bore is minimized.

* * * * *